United States Patent [19]

Hortin

[11] Patent Number: 4,861,865

[45] Date of Patent: Aug. 29, 1989

[54] NOVEL ANTITHROMBIN PEPTIDE

[75] Inventor: Glen L. Hortin, St. Louis, Mo.

[73] Assignee: Washington University, St. Louis, Mo.

[21] Appl. No.: 299,576

[22] Filed: Jan. 23, 1989

[51] Int. Cl.$^4$ .................... A61K 37/02; C07K 7/10
[52] U.S. Cl. .................................................. 530/326
[58] Field of Search ........................... 530/326; 514/13

[56] References Cited

U.S. PATENT DOCUMENTS

| | | | |
|---|---|---|---|
| 4,528,189 | 7/1985 | Lederis et al. | 530/324 |
| 4,533,654 | 8/1985 | Lederis et al. | 530/324 |
| 4,649,132 | 3/1987 | Zimmermann et al. | 530/324 |
| 4,654,302 | 3/1987 | Fritz et al. | 530/324 |
| 4,668,662 | 5/1987 | Tripier | 530/324 |
| 4,767,742 | 8/1988 | Dodt et al. | 530/324 |
| 4,791,100 | 12/1988 | Kramer et al. | 530/324 |
| 4,801,576 | 1/1989 | Fritz et al. | 514/12 |

OTHER PUBLICATIONS

Blinder et al., Biochemistry 27, 752–759 (1988).
Hortin et al., J. Biol. Chem. 261(34), 15827–15830 (1986).
Tollefsen et al., J. Biol. Chem. 257, 2162–2169 (1982).
Parker and Tollefsen, J. Biol. Chem. 260, 3501–3505 (1985).
Hortin et al., Am. J. Clin. Pathol. 89, 515–517 (1988).

Primary Examiner—Lester L. Lee
Attorney, Agent, or Firm—Scott J. Meyer; James W. Williams, Jr.

[57] ABSTRACT

A novel synthetic peptide with potent antithrombin activity is provided which has the following amino acid sequence:

1                                                                                              11
Gly—Glu—Glu—Asp—Asp—Asp—Tyr—Leu—Asp—Leu—Glu—

12                                                                                             22
Lys—Ile—Phe—Ala—Glu—Asp—Asp—Asp—Tyr—Ile—Asp.

1 Claim, 1 Drawing Sheet

NOVEL ANTITHROMBIN PEPTIDE

BACKGROUND OF THE INVENTION

This invention relates to a novel peptide having potent antithrombin activity and, more particularly, to a synthetic peptide analogous to residues 54–75 of heparin cofactor II.

Heparin cofactor II (HCII) is an inhibitor of thrombin in plasma that is activated by dermatan sulfate or heparin. It is a 65,600 dalton glycoprotein member of the serpin (serine protease inhibitor) superfamily. The full sequence of 480 amino acids of the mature protein is disclosed by Blinder et al., *Biochemistry* 27, 752–759 (1988).

A short internal repeat amino acid sequence (Glu-Asp-Asp-Asp-Tyr-X-Asp, in which X=Ile or Leu) within HCII, beginning with Glu-56 and Glu-69, respectively, has been identified by Hortin et al., *J. Biol. Chem.* 261 (34), 15827–15830 (1986). These sequences flank two tyrosine residues at positions 60 and 73, respectively, which were shown to be sulfated in a human hepatoma-derived cell line (HepG2).

Further background information on HCII can be had by reference to the following illustrative papers: Tollefsen et al., *J. Biol. Chem.* 257, 2162–2169 (1982); Parker and Tollefsen, *Ibid.* 260, 3501–3505 (1985); and Hortin et al., *Am. J. Clin. Pathol.* 89, 515–517 (1988).

BRIEF DESCRIPTION OF THE INVENTION

In accordance with the present invention a novel synthetic peptide is provided which has potent antithrombin activity. This synthetic peptide has the following amino acid sequence:

```
1                                              11
Gly—Glu—Glu—Asp—Asp—Asp—Tyr—Leu—Asp—Leu—Glu—

12                                             22
Lys—Ile—Phe—Ala—Glu—Asp—Asp—Asp—Tyr—Ile—Asp.
```

The novel 22-residue peptide is analogous to residues 54–75 of human heparin cofactor II (HCII) except that Ser-68 is replaced by Ala (residue 15 in the present peptide). For convenience, this novel peptide can also be designated HCII(54–75)[Ser(68)→Ala]. It has been found that this novel peptide potently inhibits thrombin's clotting activity but not its amidolytic activity versus small chromogenic substrates. This finding of inhibitory activity by binding to a noncatalytic site is unlike most proteinase inhibitors which complex with the active site of the enzyme. See, for example, Travis and Salvesen, *Ann. Rev. Biochem.* 52, 655–710 (1983).

The potent antithrombin activity of the 22-residue synthetic peptide was further demonstrated by comparison with tryptic fragments of 12 and 10 residues prepared from the parent peptide but which had little anticlotting activity.

The synthetic thrombin inhibitor of the present invention also provides a novel molecular probe for investigating the specificity of thrombin's interactions with inhibitors and substrates.

DETAILED DESCRIPTION OF THE INVENTION

Figure 1:
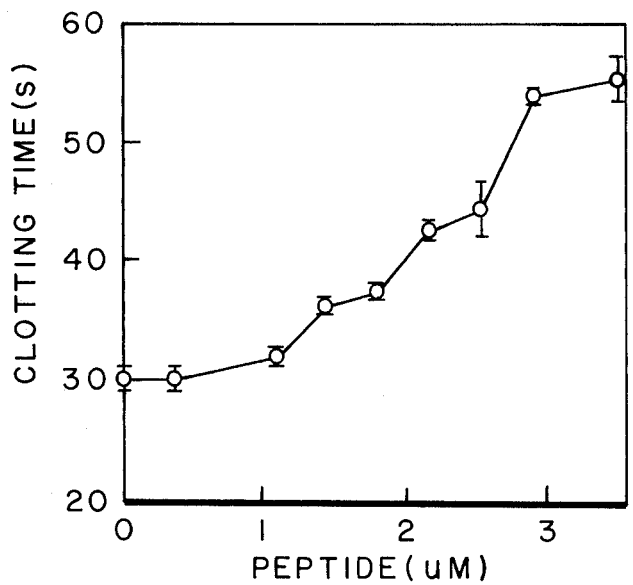

While the specification concludes with claims particularly pointing out and distinctly claiming the subject matter regarded as forming the present invention, it is believed that the invention will be better understood from the following detailed description of preferred embodiments taken in conjunction with the accompanying drawings in which:

FIG. 1 is a graphical representation which shows inhibition of fibrinogen clotting by the novel 22-residue synthetic peptide. Fibrinogen clotting times (S=seconds) in the presence of varying concentrations ($\mu M$) of the peptide were determined with a fibrometer following addition of thrombin. Each concentration of peptide was assayed in triplicate. Error bars indicate standard deviations.

Figure 2:
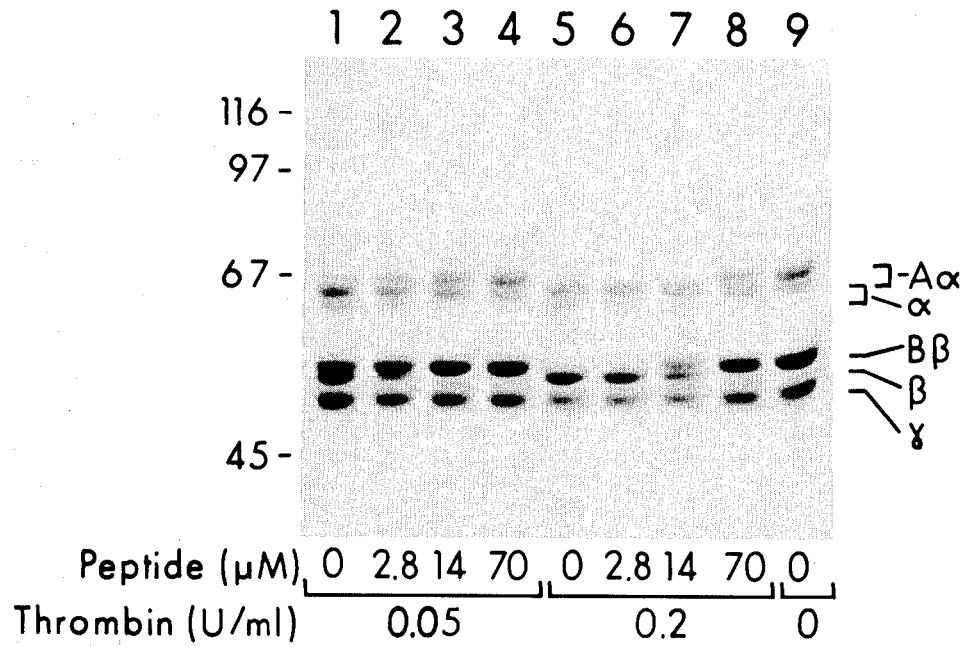

FIG. 2 is a gel pattern which shows inhibition by the peptide of FIG. 1 of thrombin's cleavage of fibrinogen. Thrombin was added in the indicated amounts (U/ml) to solutions of fibrinogen and varying amounts ($\mu M$) of the peptide. After incubation for 30 minutes, clots were solubilized in sample buffer and aliquots were analyzed by sodium dodecylsulfate polyacrylamide gel electrophoresis. The mass of molecular weight markers in kDa and the identities of fibrinogen chains are indicated on the left and right sides, respectively.

The novel 22-residue synthetic peptide of this invention can be prepared by known solution and solid phase peptide synthesis methods. Thus, in accordance with conventional solution phase peptide synthesis, the peptide chain can be prepared by a series of coupling reactions in which the constituent amino acids are added to the growing peptide chain in the desired sequence. The use of various N-protecting groups, e.g., the carbobenzyloxy group or the t-butyloxycarbonyl group (BOC), various coupling reagents, e.g., dicyclohexylcarbodiimide or carbonyldimidazole, various active esters, e.g., esters of N-hydroxyphthalimide or N-hydroxy-succinimide, and various cleavage reagents, e.g., trifluoroacetic acid, HCL in dioxane, boron-tris-(trifluoroacetate) and cyanogen bromide, and reaction in solution with isolation and purification of intermediates is well-known classical peptide methodology.

The preferred peptide synthesis method follows conventional Merrifield solid-phase procedures. See Merrifield, *J. Amer. Chem. Soc.* 85, 2149–54 (1963) and *Science* 150, 178–85 (1965). This procedure, though using many of the same chemical reactions and blocking groups of classical peptide synthesis, provides a growing peptide chain anchored by its carboxy terminus to a solid support, usually cross-linked polystyrene, styrenedivinylbenzene copolymer or p-methylbenzhydrylamine polymer. This method conveniently simplifies the number of procedural manipulations since removal of the excess reagents at each step is effected simply by washing the polymer.

Further background information on the established solid phase peptide synthesis procedure can be had by reference to the treatise by Stewart and Young, "Solid Phase Peptide Synthesis," W. H. Freeman & Co., San Francisco, 1969, and the review chapter by Merrifield in *Advances in Enzymology* 32, pp. 221–296, F. F. Nold, Ed., Interscience Publishers, New York, 1969; and Erickson and Merrifield, *The Proteins*, Vol. 2, p. 255 et seq. (ed. Neurath and Hill), Academic Press, New York, 1976.

In order to illustrate specific preferred embodiments of the invention in greater detail, the following exemplary laboratory preparative work was carried out.

Example

Solid phase peptide synthesis was carried out to provide a novel 22-residue synthetic peptide having the following amino acid sequence:

1                                                               11
Gly—Glu—Glu—Asp—Asp—Asp—Tyr—Leu—Asp—Leu—Glu—

12                                                              22
Lys—Ile—Phe—Ala—Glu—Asp—Asp—Asp—Tyr—Ile—Asp.

Materials and Methods

Materials: Reagents were obtained from the following sources: t-butyloxycarbonyl amino acids from Bachem, t-butyloxycarbonyl-L-($\beta$-benzyl)-aspartic acid phenylacetamidomethyl resin from Applied Biosystems, solvents from Burdick & Jackson, trifluoroacetic acid from Pierce Chemical, human thrombin, bovine thrombin, and Ancrod (protease from venom of Agkistrodon rhodostoma) from Sigma Chemical, human fibrinogen from Helena, 1,000 U/ml solution of heparin from Organon, trypsin (treated with tosylphenylalaninylchloromethyl ketone) from Worthington Biochemicals, and chromogenic substrates S-2366 (pyroglutamylprolylarginyl-para-nitroanilide) and S-2288 (D-isoleucylprolylarginyl-para-nitroanilide) from Helena.

Peptide Preparation: Peptide synthesis was performed using an Applied Biosystems 430A synthesizer. Coupling steps employed activation of protected amino acids as their symmetric anhydrides. Sidechain protection of $\alpha$-N-t-butoxycarbonyl-blocked amino acids was effected by the following groups: O-benzyl for Asp, Glu; O-orthobromobenzyloxycarbonyl for Tyr; ortho-chlorobenzyloxycarbonyl for Lys. Deprotection of the synthetic peptide and cleavage from the resin were performed by Immuno-Dynamics Inc. using anhydrous HF. The peptide was purified by reverse-phase HPLC using a 1×25 cm Vydac 218TP octadecylsilica column with a gradient of increasing acetonitrile in 0.05% trifluoroacetic acid. Tryptic peptides were prepared by cleaving 60 mg of peptide with 1 mg trypsin in 100 ml $NH_4HCO_3$. The digest was ultrafiltered through a Centricon-10 unit (Amicon) to remove the trypsin. The two tryptic peptides were purified by reverse-phase HPLC. Purified peptides were prepared as aqueous solutions for assays of activity. Compositions of peptides and concentrations of peptide solutions were determined by vapor-phase hydrolysis with 6N HCl for 24 h at 110° C. Amino acids were quantitated with a Beckman 6300 analyzer, with standardization of recovery using a norleucine internal standard. The composition of the novel 22-residue synthetic peptide thus prepared was: Asp 8.0, Thr 0.0, Ser 0.0, Glu 4.0, Pro 0.0, Gly 1.0, Ala 1.1, Val 0.1, Met 0.0, Ile 1.8, Leu 1.9, Tyr 1.4, Phe 1.0, His 0.0, Lys 1.0, Arg 0.0. All values were within 0.2 of expected theoretical integer values, except the value for Tyr is low due to losses during hydrolysis. The determined $\epsilon_{280}=2,380$ in water at 24° C. and theoretical $M_r=2,638$ for the novel 22-residue synthetic peptide.

Fibrinogen Clotting Assays: Peptides were mixed with a solution of fibrinogen and clotting was initiated by addition of thrombin to a concentration of 0.4 U/ml. The total volume was 0.25 ml with a final composition of 1 mg/ml fibrinogen, 125 mM NaCl, 10 mM Hepes, pH 7.4, 6 mM sodium citrate, 10 mM $CaCl_2$, and 1% polyethylene glycol. All reagents were equilibrated to 37° C. before mixing. The endpoint of clotting was established using a Precision fibrometer with an electromechanical probe. Clotting times were related to a standard curve of clotting times versus thrombin concentration.

Amidolytic Assays of Thrombin: Aliquots of thrombin were added to a solution containing varying amounts of synthetic peptide and 0.2 mM chromogenic substrate (S-2366 or S-2288) in 140 mM NaCl, 10 mM Hepes, pH 7.4, 1 mg/ml polyethylene glycol. Hydrolysis of the substrate at room temperature was monitored at 405 nm with a Hitachi U-2000 spectrophotometer.

Fibrinogen Cleavage Assay: Inhibition of thrombin's cleavage of fibrinogen was assessed by including varying amounts of synthetic peptide in 0.1 ml reactions containing 1 mg/ml fibrinogen and 0.005–0.1 U/ml thrombin. Final ionic conditions were: 130 mM NaCl, 10 mM Hepes adjusted to pH 7.4 with NaOH, and 6 mM sodium citrate. Reactions were incubated for 30 min at 37° C. Resulting clots were solubilized by adding an equal volume of 4% sodium dodecylsulfate, 10% 2-mercaptoethanol, 20% glycerol and heating the mixture for 2 min at 100° C. Aliquots (60 $\mu$l) of each sample were analyzed by polyacrylamide gel electrophoresis using the system of Laemmli as in previous work by Hortin et al., J. Biol. Chem. 261, 15827–15830 (1986). Protein bands in gels were visualized by staining with 0.1% Coomassie brilliant blue R.

Results

The novel 22-residue synthetic peptide, HCII(54–75)-[Ser(68)→Ala], was found to be an effective inhibitor of thrombin's clot-forming activity in a system containing purified fibrinogen and human thrombin (FIG. 1). Measurements of clotting time showed progressive inhibition of clotting by increasing amounts of peptide. Comparison of these results to a standard curve of thrombin concentration versus clotting time indicated that 50% inhibition of thrombin's effect was produced by a peptide concentration of 2.8 $\mu$M. (According to the standard curve of thrombin concentration, addition of half the standard amount of thrombin to the assay system yielded clotting in 54 sec.)

Tryptic fragments of 12 and 10 residues, prepared from the 22-residue synthetic peptide, had little anticlotting activity compared with the parent peptide. No significant changes in clotting time were produced by concentrations of tryptic peptides 10-fold higher than the $IC_{50}$ of the parent peptide. Results with the tryptic peptides thus did not localize functional sites in the 22-residue peptide. However, the results with the tryptic peptides served as a control for nonspecific effects of peptides added to the system. Heparin added to a final concentration of 10 U/ml also had no effect on clotting time in this system, and this served an important control that the fibrinogen preparation did not contain significant amounts of HCII, which might be activated by polyanions such as the synthetic peptide.

Clotting of fibrinogen by the snake venom proteinase, Ancrod, was not affected by addition of the 22-residue synthetic peptide, even at a concentration of 20 $\mu$M (Table 1). This result indicated that changes in clotting times induced by the synthetic peptide were not due to interference with fibrin polymerization, and that the inhibitory effect was selective for thrombin.

Although the 22-residue synthetic peptide inhibited thrombin's action in the clotting assay, the peptide, even at relatively high concentrations, had little effect on thrombin activity measured with two chromogenic substrates. In the presence of 14 µM synthetic peptide, action of thrombin on the substrate S-2366 under the conditions described in Materials and Methods, above, yielded a rate of hydrolysis of 8.2±0.2 µmol/L min (mean±S.D. for triplicate analyses) and 8.2±0.1 µmol/L min without peptide. Similar results were obtained with the substrate S-2288; the rate of hydrolysis was 10.1±1.1 µmol/L min with 14 µM peptide and 9.7±0.3 µmol/L min for control reactions. These results indicated that the peptide was not blocking thrombin's active site. The peptide's inhibition of clotting must then result from binding to a noncatalytic site on thrombin so as to impede interactions with the larger physiological substrate, fibrinogen.

TABLE 1

Clotting activity of Ancrod:
Lack of Effect of HCII(54-75)[Ser(68) → Ala]

Clotting of fibrinogen by Ancrod was determined using a fibrometer. Varying amounts of ancrod were assayed in duplicate to standardize clotting time versus activity. Clotting times in the presence of peptide HCII(54-75)[Ser(68) → Ala] are shown as the mean ± standard deviation (N = 4).

| Ancrod U/ml | HCII(54-75)-[Ser(68) → Ala] µM | Clotting time seconds |
|---|---|---|
| 0.10 | 0 | 24.5 ± 1.6 |
| 0.10 | 10 | 25.2 ± 0.9 |
| 0.10 | 20 | 25.5 ± 0.5 |
| Standards | | |
| 0.05 | 0 | 43.9 |
| 0.10 | 0 | 24.5 |
| 0.20 | 0 | 16.0 |
| 0.40 | 0 | 10.5 |

The effects of the 22-residue synthetic peptide on thrombin's cleavage of fibrinogen was assessed directly by polyacrylamide gel electrophoresis to determine whether thrombin's release of fibrinopeptide A from the α-chain and fibrinopeptide B from the β-chain were inhibited in parallel (FIG. 2). Excision of the fibrinopeptides decreased the apparent molecular weight of the α and β-chains by about 2,000. The Aα-chain of the fibrinogen used in this test is represented by two bands (lane 9), both of which were converted by thrombin to products about 2,000 daltons smaller (lanes 1 and 5). The Bβ-chain likewise was converted to the slightly smaller β-chain although higher concentrations of thrombin are required to complete this cleavage efficiently. Thrombin is known to act more rapidly on the Aα-chain so that, at low concentrations of thrombin, the Aα-chain is cleaved preferentially. At higher concentrations of thrombin both the Aα and Bβ-chains are cleaved. The 22-residue peptide inhibited the ability of thrombin to cleave both the Aα and Bβ-chains (lanes 2-4 and 6-8). This test indicates that, even though the peptide does not block thrombin's active site, it inhibits thrombin's excision of both fibrinopeptides from fibrinogen.

Amino acids are shown herein by standard three letter abbreviations as follows:

| Abbreviated Designation | Amino Acid |
|---|---|
| Ala | Alanine |
| Cys | Cysteine |
| Asp | Aspartic acid |
| Glu | Glutamic acid |
| Phe | Phenylalanine |
| Gly | Glycine |
| His | Histidine |
| Ile | Isoleucine |
| Lys | Lysine |
| Leu | Leucine |
| Met | Methionine |
| Asn | Asparagine |
| Pro | Proline |
| Gln | Glutamine |
| Arg | Arginine |
| Ser | Serine |
| Thr | Threonine |
| Val | Valine |
| Trp | Tryptophan |
| Tyr | Tyrosine |

Various other examples will be apparent to the person skilled in the art after reading the present disclosure without departing from the spirit and scope of the invention. It is intended that all such other examples be included within the scope of the appended claims.

What is claimed is:

1. A novel synthetic peptide with antithrombin activity having the following amino acid sequence:

1                                                                                   11
Gly—Glu—Glu—Asp—Asp—Asp—Tyr—Leu—Asp—Leu—Glu—

12                                                                                 22
Lys—Ile—Phe—Ala—Glu—Asp—Asp—Asp—Tyr—Ile—Asp.

* * * * *